(12) United States Patent
Lerner et al.

(10) Patent No.: US 6,197,331 B1
(45) Date of Patent: *Mar. 6, 2001

(54) PHARMACEUTICAL ORAL PATCH FOR CONTROLLED RELEASE OF PHARMACEUTICAL AGENTS IN THE ORAL CAVITY

(75) Inventors: E. Itzhak Lerner, Petah Tikva; Vered Rosenberger, Givataim; Moshe Flashner, Petah Tikva, all of (IL)

(73) Assignee: Perio Products Ltd., Jerusalem (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/899,775

(22) Filed: Jul. 24, 1997

(51) Int. Cl.[7] ........................................ A61F 13/02
(52) U.S. Cl. ........... 424/448; 424/449; 424/443; 424/447; 602/3; 602/41; 604/890.1
(58) Field of Search ................ 424/443, 447, 424/448, 449; 602/3, 41; 604/890.1

(56) References Cited

U.S. PATENT DOCUMENTS

| | | | |
|---|---|---|---|
| 3,255,018 | 6/1966 | Comollo | 99/135 |
| 3,679,792 | 7/1972 | Litchfield et al. | 424/48 |
| 3,972,995 | 8/1976 | Tsuk et al. | 424/28 |
| 4,059,686 | 11/1977 | Tanaka et al. | 424/19 |
| 4,386,106 | 5/1983 | Merritt et al. | 426/5 |
| 4,524,824 | 6/1985 | Shimokobe et al. | 106/35 |
| 4,568,535 | 2/1986 | Loesche | 424/19 |
| 4,597,959 | 7/1986 | Barr | 424/19 |
| 4,632,824 | 12/1986 | Hirota et al. | 424/49 |
| 4,772,470 | 9/1988 | Inoue et al. | 424/435 |
| 4,829,056 | 5/1989 | Sugden | 514/54 |
| 4,876,092 | 10/1989 | Mizobuchi et al. | 424/435 |
| 4,900,554 | 2/1990 | Yanagibashi et al. | 424/448 |
| 4,915,948 | 4/1990 | Gallopo et al. | 424/435 |
| 4,948,580 | 8/1990 | Browning | 424/78 |
| 4,994,276 | 2/1991 | Baichwal et al. | 424/440 |
| 5,002,769 | 3/1991 | Friedman | 424/422 |

(List continued on next page.)

FOREIGN PATENT DOCUMENTS

| | | |
|---|---|---|
| 0 223 245 | 5/1987 | (EP) . |
| 4-38726 | 6/1992 | (JP) . |
| WO 91/19486 | 12/1991 | (WO) . |
| WO 97/02020 | 1/1997 | (WO) . |

OTHER PUBLICATIONS

Alvarez–Fuentes, J. et al., "Morphine Polymeric Coprecipitates for Controlled Release: Elaboration and Characterization," *Drug Dev. and Indust. Pharm.* 20(15):2409–2424 (1994).

Bircher, A.J. et al., "Adverse skin reactions to nicotine in a transdermal therapeutic system," *Contact Dermatitis* 25(4):230–236 (1991).

Dévay, A. and I. Rácz, "Vizes Eudragit tartalmú diszperziók alkalmazása szabályozott hatóanyagleadású orális antihisztamin készitmények elöállitására," *Acta Pharmaceutica Hungarica* 58(4):166–172 (1988). with English language abstract, p. 172.

Friend, D.R., "Polyacrylate resin microcapsules for taste masking of antibiotics," *J. Microencap.* 9(4):469–480 (1992).

*Primary Examiner*—S. Mark Clardy
*Assistant Examiner*—Michael A. Williamson
(74) *Attorney, Agent, or Firm*—D'Vorah Graeser (57) ABSTRACT

The invention is directed to a controlled-release solid composition for the oral cavity or "pharmaceutical oral patch" that adheres to hard dental surfaces, such as teeth and dentures, and releases an active pharmaceutical agent into the oral cavity. Release of the agent is for a predetermined period of time and at a predetermined sustained concentration. The site of action of the agent is local or systemic.

19 Claims, 1 Drawing Sheet a. SIDE PROFILE OF THE DENTAL PATCH b. VIEW FROM ABOVE

A – CAVITY FOR THE GLUE
B – BODY OF THE DENTAL PATCH

U.S. PATENT DOCUMENTS

| | | | |
|---|---|---|---|
| 5,023,082 | 6/1991 | Friedman et al. | 424/426 |
| 5,077,051 | 12/1991 | Gallopo et al. | 424/435 |
| 5,081,157 | 1/1992 | Pomerantz | 514/781 |
| 5,096,717 | 3/1992 | Wirth et al. | 424/490 |
| 5,116,603 | 5/1992 | Friedman | 424/53 |
| 5,128,143 | 7/1992 | Baichwal et al. | 424/464 |
| 5,135,757 | 8/1992 | Baichwal et al. | 424/465 |
| 5,139,768 | 8/1992 | Friedman | 424/45 |
| 5,160,737 | 11/1992 | Friedman et al. | 424/401 |
| 5,288,497 | 2/1994 | Stanley et al. | 424/440 |
| 5,288,498 | 2/1994 | Stanley et al. | 424/440 |
| 5,330,746 | 7/1994 | Friedman et al. | 424/49 |
| 5,330,761 | 7/1994 | Baichwal | 424/469 |
| 5,403,577 | 4/1995 | Friedman | 424/45 |
| 5,438,076 | 8/1995 | Friedman et al. | 514/772.6 |
| 5,446,070 | 8/1995 | Mantelle | 514/772.6 |
| 5,639,795 | 6/1997 | Friedman et al. | 514/772.6 |
| 5,648,399 | 7/1997 | Friedman et al. | 514/772.6 |

OTHER PUBLICATIONS

Govender, T. et al., "Microencapsulated Eudragit® RS30D–coated controlled–release pellets: the influence of dissolution variables and topographical evaluation," *J. Microencap.* 14(1):1–13 (Jan.–Feb. 1997).

Kaura, S. et al., "A Study of the Effects of Sucrose Concentration, Lacquer Concentration and Coating Time on the Formulation of Stable and Effective Carbenicillin Indanyl Sodium Microcapsules," *Drug Dev. and Indust. Pharm.* 14(7):925–937 (1988).

Kim, N.–S. et al., "Preparation and Evaluation of Eudragit Gels. III: Rectal Gel Preparations for Sustained Release of Pentoxifylline," *J. Pharm. Sci.* 81(6):537–540 (1992).

Lee, B.–J. and G.–H. Min, "Oral controlled release of melatonin using polymer–reinforced and coated alginate beads," *Intl. J. Pharm.* 144(1):37–46 (Nov. 1996).

Morishita, I. et al., "Controlled Release Microspheres Based on Eudragit L100 for the Oral Administration of Erythromycin," *Drug Design and Delivery* 7(4):309–319 (1991).

Morishita, M. et al., "Novel oral microspheres of insulin with protease inhibitor protecting from enzymatic degradation," *Intl. J. Pharm.* 78(1):1–7 (1992).

Nagai, T., "Buccal/Gingival Drug Delivery Systems," *J. Controlled Release* 6:353–360 (1987).

Narisawa, S. et al., "An Organic Acid–Induced Sigmoidal Release System for Oral Controlled–Release Preparations. 2. Permeability Enhancement of Eudragit RS Coating Led by the Physicochemical Interactions with Organic Acid," *J. Pharm. Sci.* 85(2):184–188 (Feb. 1996).

Ndesendo, V.M.K. et al., "Microencapsulation of chloroquine diphosphate by Eudragit RS100," *J. Microencap.* 13(1):1–8 (Jan.–Feb. 1996).

Prantera, C. et al., "Oral 5–Aminosalicyclic Acid (Asacol) in the Maintenance Treatment of Crohn's Disease," *Gastroenterology* 103(2):363–368 (1992).

Sentrakul, P. et al., "Adverse skin reactions to transdermal oestradiol in tropical climate. A comparative study of skin tolerance after using oestradiol patch and gel in Thai postmenopausal women," *Maturitas* 13(2):151–154 (1991).

Tirosh, B. et al., "The effect of Eudragit RL–100 on the mechnical and mucoadhesion properties of polycarbophil dosage forms," *J. Controlled Release* 45(1):57–64 (Feb. 1997).

Venkatarum, S. and M. Khohlokwane, "Microencapsulation of an iron chelator for sustained release and crystal habit modification," *J. Microencap.* 13(5):519–525 (Sep.–Oct. 1996).

Vyas, S.P. et al., "Enteric spherules diastase in enzyme preparations," *J. Microencap.* 8(4):447–454 (1991).

Dialog File 351 (Derwent World Patent Index) Acc. No. 86–159568/198625, English language abstract for Document AN1 (JP 4–38726) 1992.

El–Nakeeb, M.A. and R.T. Yousef, "Influence of various materials on antibiotics in liquid pharmaceutical preparations," *Acta Pharmaceutica Suecica* 5(1):1–8 (1968).

a. SIDE PROFILE OF THE DENTAL PATCH b. VIEW FROM ABOVE

A — CAVITY FOR THE GLUE
B — BODY OF THE DENTAL PATCH

Figure 1

PHARMACEUTICAL ORAL PATCH FOR CONTROLLED RELEASE OF PHARMACEUTICAL AGENTS IN THE ORAL CAVITY

BACKGROUND OF THE INVENTION

1. Field of the Invention

The invention is directed to a sustained- or controlled-release solid composition for the oral cavity or "pharmaceutical oral patch" that adheres to hard dental surfaces, such as teeth and dentures, and releases a pharmaceutical agent. Release of the agent is for a predetermined period of time and at a predetermined concentration. The site of action of the agent is topical, local or systemic. The invention is also directed to suitable polymers for the pharmaceutical oral patch, in particular the polymers known as Eudragit™. The patch can comprise a single adherent release layer or a non-adherent layer adhered in the oral cavity by a separate adherent layer.

2. Related Art

The advantages of controlled-release products are well-known in the pharmaceutical field and include the ability to maintain a desired level of medicament over a desired period of time while increasing patient compliance by reducing the number of administrations necessary to achieve the same level.

Oral controlled-release delivery systems should ideally be adaptable so that release rates and profiles can be matched to physiological and chronotherapeutic requirements. The art describes free forms, such as sublingual tablets, troches, and buccals. In addition to non-attached oral sustained- or controlled-release forms, other forms are designed to adhere to the oral mucosa and deliver an active pharmaceutical agent either directly into the oral mucosa, or into the saliva. Ointments and other sticky adhering compositions also have been used. The active ingredient in all these forms can act locally or systemically.

U.S. Pat. No. 4,829,056 describes a buccal tablet consisting of etorphine, at least one monosaccharide, disaccharide or mixture thereof, and a mixture of xanthan gum and locust bean gum in a weight ratio of 3:1 to 1:1, wherein the total weight of the mono- and/or disaccharides relative to the combined weight of xanthan and locust bean gums is in the ratio of 20:1 to 3:1. The buccal tablet is intended to be placed between the gingival surface of the jaw and the buccal mucosa where it gels to produce a soft hydrated tablet which may be retained in position so as to provide release of etorphine for up to two hours. The buccal tablet is said to provide improved bioavailability.

U.S. Pat. No. 4,948,580 describes a bioadhesive composition which may be employed as an oral drug delivery system and includes a freeze-dried polymer mixture formed of the copolymer poly(methyl vinyl ether/maleic anhydride) and gelatin dispersed in an ointment base. This composition is said to be useful to deliver active ingredients such as steroids, antifungal agents, and antibacterial agents, to the oral mucosa.

U.S. Pat. No. 4,597,959 describes a cosmetic breath freshener composition in wafer form which is said to have slow release properties. The composition includes a multiplicity of microencapsulated liquid droplets of flavoring material contained in an adhesive base.

U.S. Pat. No. 5,077,051 describes bioadhesive microcapsules which comprise xanthan gum, locust bean gum, a bulking agent and an active agent. The microcapsules are said to be useful for delivering buffering agents to the oral cavity for anticarious purposes. The microcapsules are prepared by preparing a hot aqueous solution or suspension of the active agent; adding xanthan gum, locust bean gum and a bulking agent to form a viscous solution; and then (a) cooling and then drying the viscous solution to obtain a solid material which is then formed into microcapsules, or (b) spray-drying the viscous solution to form the microcapsules.

U.S. Pat. No. 4,915,948 describes a tablet which is said to have improved adhesion to mucous membranes. The tablet includes a water soluble biopolymer selected from xanthan gum, a pectin and mixtures thereof, and a solid polyol having a solubility at room temperature in water greater than about 20 g/100 g solution.

U.S. Pat. Nos. 4,994,276, 5,128,143, and 5,135,757, describe a controlled release excipient comprised of synergistic heterodisperse polysaccharides (e.g., a heteropolysaccharide, such as xanthan gum in combination with a polysaccharide gum capable of cross-linking with the heteropolysaccharide, such as locust bean gum) that is capable of processing into oral solid dosage forms using either direct compression, following addition of drug and lubricant powder, conventional wet granulation, or a combination of the two. Release of the medicament from the formulations is reported to proceed according to zero-order or first-order mechanisms.

U.S. Pat. No. 4,059,686 describes a pharmaceutical preparation for oral cavity administration characterized by being a mixture of a pharmacologically active agent, a pharmaceutical carrier, and sodium polyacrylate in conventional dosage form. It adheres strongly to a local site and dissolves gradually over a prolonged period of time, releasing appropriate amounts of the active agent. The preparation is designed to adhere to mucosal membranes.

U.S. Pat. No. 4,876,092 describes a sheet-shaped adhesive preparation comprising an adhesive layer containing, as essential components, a carboxyvinyl polymer, a water-insoluble methacrylic copolymer, a polyhydric alcohol, and a pharmaceutically active agent, and a water-impermeable and water-insoluble carrier layer containing, as essential components, a pharmaceutically active, water-insoluble, film-forming high molecular weight compound and a plasticizer, which can adhere within the oral cavity over a period of time and release an active agent. The preparation is designed to be adhered to the mucous membrane.

U.S. Pat. No. 3,972,995 describes a dosage form for buccal administration of a drug, and which is directly applicable to the interior surfaces of the mouth. The dosage form is comprised of a support member which is water-insoluble, waterproof and flexible, a moisture-activated adhesive precursor applied to one surface of the support member, and an active ingredient applied to the central portion of the support member, either directly or dispersed in a matrix. The dosage form is applied directly to the interior surface of the mouth. Contact with saliva activates the adhesive and causes the support member to adhere to the interior surface of the mouth, thereby exposing the active ingredient to a limited area of the oral mucosa while isolating the active ingredient from the remainder of the oral environment.

U.S. Pat. No. 5,330,761 describes a controlled release bioadhesive tablet which includes a locally active agent, a heterodisperse gum matrix, and a pharmaceutically acceptable diluent. The final product adheres to mucous membranes and releases the locally active agent over a desired period of time.

Nagai, T. et al. (J. Cont. Rel. 6:353 (1987)) describes a sustained-release tablet capable of sticking tightly to human gingiva and not the cheek mucosa. Further described is a self-administered plaster with a water-impermeable backing layer (film).

U.S. Pat. No. 4,772,470 discloses an oral bandage comprising a soft adhesive film comprising a mixture of polycarboxylic acid and/or a polycarboxylic acid anhydride and a vinyl acetate polymer in a compatible state, and an oral preparation comprising such an oral bandage having incorporated therein a topical drug. The oral bandage or preparation is reported to exhibit strong adhesion of long duration when applied to the oral mucosa or teeth. This patent purports to teach a composition for topical administration of pharmaceutically active agents. It is drawn primarily to the use of anesthetic compositions, but may comprise other agents as well. The composition comprises the active agent in a pharmaceutically acceptable solvent, and in an admixture also includes a bioadhesive. This patent, however, does not teach the use of a sustained-release composition wherein the composition can be attached to a tooth or other dental surface by separate adhesive.

U.S. Pat. No. 4,900,554 describes an adhesive device for application to body tissue having an adhesive layer and a backing layer positioned over one side of the adhesive layer. The adhesive layer includes one or more acrylic acid polymers having adhesive properties upon dissolution or swelling in water and at least one water-insoluble cellulose derivative. The backing layer is water-insoluble or sparingly water-soluble. This patent discloses a composition comprising the active agent in an admixture that also includes a bioadhesive. Further, it includes a backing layer so that the adhesive does not adhere to adjacent areas. Further, the patent does not teach the use of a sustained-release composition which can be attached to a tooth or other dental surface by a separate adhesive.

U.S. Pat. No. 5,446,070 relates to compositions and methods for topical administration of pharmaceutically active compounds and specifically to anesthetic compounds for topical administration. The invention is a flexible bioadhesive composition for topical application comprising a pharmaceutically active agent, a solvent and a plasticizer, in admixture with a polysaccharide bioadhesive carrier, wherein the composition is substantially free of water, substantially water-insoluble, and wherein the pharmaceutically active agent is present in a non-crystallized form. The patent discloses that an exceptionally high loading of anesthetic agents can be added to a carrier without loss of the adhesive properties, so that more rapid delivery of an anesthetic agent to a tissue without substantial crystallization of the agent can occur. The reference discloses the use of the composition for topical administration to hard tissue such as teeth. However, the active agent is an admixture with the adhesive agent. The patent does not disclose a drug delivery device attached by means of an adhesive agent.

European Patent Application 223 245 discloses a curable composition containing methacrylate monomers and a polymerization initiator for application to teeth and having the property of in situ polymerization to form a hardened filler. The reference discloses the use of such filler in combination with an active agent, thereby releasing the active agent from the hardened filler. These compositions are not used, however, to form a sustained release device attached by means of an adhesive composition.

Furthermore, each of the above-cited references further discuss sustained-release compositions, many of which can be used to release a pharmaceutically active agent in the oral cavity.

Several problems are associated with controlled-release or sustained-release formulations in the oral cavity.

A major problem is providing prolonged release at effective concentrations. For example, fungal infections beginning in the mouth and then entering other parts of the body are life-threatening to immuno-compromised patients. It is thus desirable to release antifungal agents on an ongoing basis. However, it is very difficult to achieve.

Buccal tablets and sublingual tablets are pharmaceutical preparations primarily intended for systemic effect. These tablets are placed between the cheek and gingival or under the tongue and allowed to dissolve slowly. The drugs absorbed through the oral mucous membrane enter directly, not through the portal circulation but through the systemic circulation. An advantage of these tablets is in the efficient absorption of the drug, because the drug is not decomposed by the liver. However, if the disintegration and dissolution of the tablet are too rapid, the object of this method of administration is not achieved.

A problem with these sustained-release devices involves the area of comfort. Patients often reject these oral sustained-release devices because they have a "foreign" feeling. As a result, these devices are often dislodged by the patient.

Recently, a tablet for stomatitis has been developed which is applicable directly to the affected region. But this preparation is also hard and has a certain thickness, and persons using it are aware of its presence. Accordingly, the tablet may be dislodged with the tongue and swallowed during eating and drinking. Therefore, it is difficult to retain within the oral cavity for a long time.

Moreover, the known preparations are usually composed of components which are soluble or disintegrable within the mouth. Thus, the pharmaceutically active agents contained in the preparations are mostly swallowed without being absorbed through the mucous membrane in the oral cavity. Thus, these preparations are not completely satisfactory as a sustained- or controlled-release preparation for the oral cavity.

In order to retard disintegration of the above said preparations, the following trials have been made without successful results as a preparation for oral cavity administration:

1. to add larger amounts of a binder, without employing a disintegrant, such as starch;
2. to add a large amount of hydrophobic lubricant, such as magnesium stearate;
3. to coat the tablet with a water-repellent substance such as wax or paraffin.

Ointments are not satisfactory for oral cavity administration because of insufficient adhesion and rather high solubility.

Mucosal patches, which demonstrate good adhesion for extended periods of time, cause adverse reactions like mucosal itching and irritation at the patch sites or even necrosis in severe cases. (*Contact-Dermatitis* 25(4):230–6 (1991); *Maturitas* 13(2):15–4 (1991).) In addition to health complications, the side effects profile of a product can lead to added therapeutic costs by requiring treatment by physicians or visits to emergency rooms.

Another problem is localized release to teeth. That is, the application of agents that are designed to be delivered to teeth, for example, tooth whiteners and desensitizing agents, are for the most part wasted because delivery is to the whole oral cavity and not local to the tooth.

Another problem is the difficulty of application of sustained release devices for the oral cavity.

Controlled Release Drug Formulations Containing Eudragit™

Eudragit™ polymers form a diverse family of polymers whose common feature is a polyacrylic or polymethacrylic backbone that is compatible with the gastrointestinal tract and which have been widely used in pharmaceutical preparations, especially as coatings for tablets. Eudragit™ polymers have been used, among other things, for controlled release of pharmaceutical agents. In most formulations, Eudragit™ is used for coating a core containing the pharmaceutical agent.

Ndesendo et al., *J. Microencap.* 13:1–8 (1996) disclosed coacervation of a highly water soluble drug using Eudragit RS-100™ as the coating material.

Benkataram et al., *J. Microencap.* 13:519–25 (1996) disclosed a sustained release formulation in which an iron chelator is microencapsulated in either Eudragit RS™, RL™, or L-90™.

Narisawa et al., *J. Pharm. Sci.* 85:184–8(1996) disclosed drug-containing beads coated with Eudragit NE-30D™.

Friend, D. R., *J. Microencap.* 9:469–80 (1992) disclosed sustained release formulations of a core drug coated with either Eudragit L-100™, S-100™ or E-100™.

Prantera et al., *Gastroenterology* 103:363–8 (1992) disclosed a delayed release formulation of ASA coated with Eudragit S™.

Morishita et al., *Drug Des. Deliv.* 7:309–19 (1991) disclosed the preparation of erythromycin microspheres using Eudragit L-100™ as the coating material to produce controlled release of the drug.

Tirosh et al., *J. Contr. Rel.* 45:57–64 (1997) disclosed the incorporation of Eudragit RL-100™ into polycarbophil to compensate for the poor mechanical properties of polycarbophil in the preparation of solid dosage forms for oral delivery of drugs.

Lee et al., *Int. J. Pharmaceut.* 144:37–46 (1996) disclosed drug containing alginate beads coated with Eudragit RS-100™ and aluminum tristearate (as a plasticizer) to create sustained-release dosage forms for melatonin.

Govender, *J. Microencap.* 14:1–13 (1997) disclosed microencapsulated Eudragit RS-30D™-coated controlled release pellets.

Morishita et al., *Int. J Pharm.* 78:1–8 (1992) disclosed Eudragit L-100™ microspheres as an oral dosage form for the release of insulin.

Kaura et al., *Drug Dev. Ind. Pharm.* 7:925–938 (1988) disclosed an oral dosage formulation containing a coating of Eudragit E-100R™.

WO/97/02020 discloses oral pharmaceutical compositions for slow release of an anti-microbial agent in which the release-controlling layer can be Eudragit RS™, RL™ or RTM™ and is also coated by Eudragit L™ or Eudragit RTM™.

WO/91/19486 discloses microspheres with a core containing drug and two or more enteric coatings, wherein the enteric coatings can be Eudragit L-100-55™ (RTM) or Eudragit E-100™ (RTM).

U.S. Pat. No. 5,096,717 discloses controlled release oral dosage forms containing a coating of Eudragit L-30D™.

Japanese Application No. 61093133 (now JP 92038726) describes a buccal tablet comprising a pharmaceutical-containing solid sandwiched between an adhesive film and a film not soluble in water, for example, Eudragit RTM™. The tablet is described as being highly adhesive to the oral cavity for long slow release of the pharmaceutical ingredient from the solid into the oral cavity. The Eudragit™ layer and the drug layer are discreet layers. There is no liquid dispersion or solid dispersion.

Alvarez-Fuentes et al., *Drug Dev. Ind. Pharm.* 20:2409 (1994) discloses co-precipitation of morphine and Eudragit L-30™ as a carrier. Chemical association between the morphine and the Eudragit L-30™ carrier is by hydrogen bonding. The polymer is neutralized using NaOH, KOH, etc.

None of the above references discloses a liquid composition containing a Eudragit™ polymer dispersed with a pharmaceutical agent, which liquid dispersion is then capable of dying to form a solid product in which the pharmaceutical agent is dispersed in the Eudragit™ polymer matrix.

However, liquid dispersions of Eudragit™ with a pharmaceutical agent, which dispersions can be dried to form a dispersion of the pharmaceutical agent in the Eudragit™ polymer have been described.

Kim et al., *J. Pharm. Sci.* 81:537–40 (1992) described a hydrogel and xerogel preparation containing a medicinal component dispersed in a gel matrix of Eudragit S™, Eudragit L™, or Eudispert™. The gel is bioadhesive in the rectum. The matrix is bioerodible. Properties of the matrix are altered with NaOH, KOH, and the like.

Vyas et al., *J. Microencap.* 8:447–54 (1991) described dispersions of diastase in Eudragit RS-100™.

Devay et al., *Acta. Pharm. Hung.* 58:166–72 (1988) described antihistamine dispersions into aqueous Eudragit™.

None of these formulations, however, has been used to achieve controlled release of a pharmaceutical agent in the oral cavity.

U.S. Pat. Nos. 5,160,737 and 5,330,746 disclose a sustained release liquid polymer composition comprising Eudragit L™, S™, RL™, or SL™ and a pharmaceutical agent. U.S. Pat. Nos. 5,160,737 and 5,330,746 use the formulation for preventing dental caries, periodontal disease, and tooth hypersensitivity by brushing or spraying the formulation onto the teeth and gingivae forming a film. Thus, the solid formulation provides controlled-release of a drug into the oral cavity. However, there is no disclosure or suggestion of forming a delivery vehicle other than the film.

Accordingly, there is a need for an oral controlled-release pharmaceutical delivery device with the following characteristics. Release can be sustained at desired concentrations for an extended desired period of time. Necrosis is avoided. Release can be localized to teeth. Application is easy and uncomplicated. Patient comfort is provided in that the device is comfortable and does not impart a "foreign" feeling to the oral cavity. Buccal absorption is facilitated, resulting in rapid systemic delivery of the released agent. Localized treatment of the oral mucosa is provided. The device is easily removable, in that it is not bonded to the attachment site (i.e., teeth) physically or chemically. Therefore, no scraping or chemical treatment is required to remove the device, although the device is available for release, holding to the site for an extended period of time (i.e., several hours).

SUMMARY OF THE INVENTION

A general object of the invention is to provide a sustained- or controlled-release composition for the oral cavity that provides release of effective amounts of one or more pharmaceutical agents in the oral cavity.

A specific object of the invention is to provide a composition that avoids necrosis in the oral cavity.

A further specific object of the invention is to provide a composition that delivers a pharmaceutical agent for local treatment of the oral cavity, throat, or esophagus.

A further specific object of the invention is to provide a composition for topical release to sites of attachment, e.g., to the teeth.

A further specific object of the invention is to provide a composition for oral release of a pharmaceutical, allowing for buccal absorption resulting in rapid systemic delivery of the released pharmaceutical.

A further specific object of the invention is to provide a composition whose application and removal is easy and uncomplicated.

A further specific object of the invention is to provide a device that feels comfortable in the mouth and thus provides the minimum possibility of being dislodged by the patient, so that the pharmaceutical agent is released for an effective period of time at the desired concentration.

A further specific object of the invention is to provide a composition for oral release of a pharmaceutical that releases the pharmaceutical by both diffusion and erosion of a matrix.

A further specific object of the invention is to provide a composition that is degradable in the oral cavity.

A further specific object of the invention is to provide a composition for the oral release of a variety of pharmaceuticals, especially for non-, poorly, or intermediately water-soluble pharmaceuticals and particularly, poorly water-soluble pharmaceuticals.

A further specific object of the invention is to provide for oral release of a pharmaceutical with an adhesive composition that will adhere to the teeth, dentures, or other hard structures of the dental cavity.

A further specific object of the invention is to provide a composition for oral release of a pharmaceutical in which the release rate of the pharmaceutical can be controlled by the method of making the composition.

A further specific object of the invention is to provide a composition that can release more than one pharmaceutical agent in the oral cavity.

A further specific object of the invention is to provide a device having advantages over a film formed in situ by providing for better control of the dose administered.

Accordingly, the inventors have designed a composition that achieves all of these objects.

Thus, the inventors have designed a composition for sustained- or controlled-release in the oral cavity of a pharmaceutically active agent contained in the composition.

The invention provides a solid sustained- or controlled-release composition that can be adhesively attached to the surface of a tooth, denture, or other hard dental structure. The composition is referred to as a "pharmaceutical oral patch."

In the pharmaceutical oral patch, an inert (non-drug-containing) adhesive composition can attach a separate drug-containing non-adhesive composition to the teeth or other hard structures, such as dentures.

Alternatively, the drug-containing composition can be self-adhesive.

In other embodiments, where the drug-containing composition in the patch is not adhesive, the adhesive composition can also contain the same or different drugs.

In a preferred embodiment, the controlled-release composition comprises at least one polymer. Whether the drug-containing composition is self-adherent, not self-adherent (requires a non-drug-containing adhesive to adhere it in the oral cavity), or if the drug-containing non-adhesive composition is attached in the oral cavity by means of an adhesive drug-containing composition, in each of these embodiments the compositions can comprise at least one polymer.

In preferred embodiments, both the adhesive and non-adhesive compositions comprise at least one polymer.

In preferred embodiments, the polymer forms a matrix in which the pharmaceutical is dispersed or embedded.

The preferred polymer for both the adhesive layer and non-adhesive layer is a methacrylic polymer and, preferably, a Eudragit™ polymer.

In a highly preferred embodiment, Eudragit S™ is the attachment adhesive.

In a highly preferred embodiment, Eudragit L-100™ is the non-adhesive drug-releasing component.

In the embodiment in which an adhesive composition attaches a separate drug-containing composition, one advantage over a system with a combined adhesive and drug-releasing layer (e.g., U.S. Pat. Nos. 4,772,470, 4,900,554 and 5,446,070) is the ability to form a new adhesive layer when the first one is damaged without the need for a new releasing layer.

In a system in which both the release layer and the adhesive layer contain an active ingredient, the separation between the two layers avoids migration of the active ingredient from the adhesive layer into the release layer and vice versa. This is preferred where the active ingredients differ between the two layers.

Either or both layers can be degradable. Thus, the entire patch can be significantly or completely degradable. This means that no significant residue remains on the tooth after the intended use (desired released active agent) so there is no need to remove a depleted patch. This includes embodiments in which the drug-releasing matrix layer is self-adherent, and also comprises embodiments in which there is more than one layer, as in the case where a non-adhesive layer is adhered to the tooth by means of a separate adhesive layer.

The minimal essential ingredients, for the non-adhesive release layer include at least one pharmaceutically active agent, at least one polymer, and at least one plasticizer. Optional ingredients include release adjusting agents, pH adjusting agents, emulsifiers, and solubility adjusting agents. In the liquid that ultimately forms this solid composition, the minimal essential ingredients include at least one polymer, at least one pharmaceutical, at least one plasticizer, and a pharmaceutically acceptable solvent.

In the adhesive layer, minimal essential components include at least one polymer. However, optional ingredients may be added, for example, plasticizer, release adjusting agent, emulsifier, pH adjusting agent, and solubility adjusting agent. A drug can be included in the adhesive layer as a minimal essential ingredient.

Where the release layer is self-adherent, the minimal essential components include at least one polymer, at least one pharmaceutical, and at least one plasticizer.

The application also provides a method for making the compositions described herein. In general embodiments of the procedure for forming the drug-releasing matrix, for acrylic or methacrylic polymers, the acrylic or methacrylic polymer is dissolved in a mixture of alcohol and water. A base is then optionally added to adjust the pH. A plasticizer is then added to the mixture to plasticize the resulting solid product. A pharmaceutical is then added, and the mixture is stirred until dissolved. The solution is then introduced into an appropriate mold and dried to form the finished product.

An essential feature is a polymer that dissolves in a pharmaceutically acceptable solvent (such as ethanol:water) and that can be plasticized to form a flexible polymer matrix when dried and then inserted in the oral cavity.

Thus, the invention provides a method for controlling the release of a given pharmaceutical from the non-adherent solid compositions described herein, as well as the adhesive drug-releasing compositions described herein.

DETAILED DESCRIPTION OF THE PREFERRED EMBODIMENTS

The invention is generally directed to a composition for the oral cavity that provides effective controlled release of a pharmaceutical agent in the oral cavity.

The invention is specifically directed to a composition that avoids necrosis in the oral cavity and related areas.

The invention is also specifically directed to a composition that delivers a pharmaceutical agent to the oral cavity, throat, or esophagus.

The invention is also specifically directed to providing topical release of a pharmaceutical confined to the teeth.

The invention is also specifically directed to a sustained- or controlled-release system for oral release of a pharmaceutical allowing for buccal absorption resulting in rapid systemic delivery of the released pharmaceutical.

The invention is also specifically directed to a controlled-release composition whose application is easy and uncomplicated.

The invention is also specifically directed to a controlled-release composition that feels comfortable in the mouth and thus provides the minimum possibility of being dislodged by the patient, so that the agent is released for an effective period of time at an effective concentration.

The invention is also specifically directed to providing a sustained- or controlled-release system for oral release of a pharmaceutical that releases the pharmaceutical by both diffusion and erosion of a matrix.

The invention is also directed to a sustained- or controlled-release composition for oral release of a pharmaceutical, wherein release can be adjusted with an agent or agents in the liquid mixture with respect to duration of release and concentration, in the oral cavity, of the released pharmaceutical.

The invention is also specifically directed to a sustained- or controlled-release system for oral release of a pharmaceutical that provides effective release for non-, poorly, or moderately water-soluble pharmaceuticals and particularly for poorly water soluble pharmaceuticals.

The invention is thus directed to a solid composition that can be adhesively attached to the surface of a tooth or other hard dental structure, and is collectively referred to herein as a "pharmaceutical oral patch."

The invention is also specifically directed to a sustained- or controlled-release composition that will self-adhere or which can be attached to the teeth, dentures, or other hard structures of the dental cavity.

The invention provides a means for delivering different drugs, one from a non-adhesive layer and the other from an adhesive layer.

The invention also provides a means of delivering drugs separately, one from a non-adhesive layer and the other from an adhesive layer.

The invention also provides a means of delivering drugs separately or delivering two separate drugs from two different adhesive layers that collectively form the patch.

Thus, several general embodiments are covered by the invention, including embodiments in which the entire patch is self-adherent, in which the patch contains a non-adhesive release layer that needs to be adhered by an adhesive layer, embodiments in which two or more drug-containing adhesive layers are contained, and embodiments in which the same or different drugs can be released from each of the layers, separately.

In its simplest embodiment, there is only one self-adherent composition, i.e., only one layer. In further complex embodiments, however, there can be more than one adherent layer. These may contain one or more of the same or different drugs. Further, more than one non-adhesive layers can be combined with one or more adhesive layers in which the drugs are one or more of the same or different drugs in each layer.

The advantages of the patch over a film formed in situ is that greater quantities of the active ingredient can be made available to the patient and therefore treatment can be provided for a longer period of time with higher amounts of the active ingredient. Also, the preformed pharmaceutical oral patch allows for better control of the dose administered than a film, allows for greater ease of use, and for improved adhesion. A premeasured dose can be applied in one application rather than having to apply multiple layers of a film-forming varnish.

The invention is also specifically directed to a sustained- or controlled-release system for oral release of a pharmaceutical in which the release rate of the pharmaceutical and the concentration of the pharmaceutical in the oral cavity can be controlled by the method of making the system.

The patch can be a self-adhesive drug-containing composition or, in preferred embodiments, an inert (not containing a drug) adhesive composition attaches a separate non-adhesive drug-containing composition to the teeth or other hard structures such as dentures. In some embodiments, the adhesive layer can also contain a drug.

Accordingly, the invention is directed to a liquid composition comprising at least one pharmaceutical and at least one polymeric component that is capable of drying to form a composition that will effectively release the pharmaceutical in the oral cavity, which itself is adhesive when dried or which can be adhered to an adhesive composition which, in turn, can adhere to the hard structures in the oral cavity.

In addition, the liquid composition can be formulated with a release-adjusting agent that affects the rate and extent (concentration) of pharmaceutical released from the solid composition in the oral cavity.

In preferred embodiments, the polymer and the drug are physically associated as a dispersion in both the liquid and solid form of the sustained-release composition. Thus, the drug is embedded in a polymeric matrix.

The preferred material for the drug-containing composition is methacrylate or acrylate. The Eudragit™ are characterized as (1) an anionic copolymer based on methacrylic acid and methylmethacrylate wherein the ratio of free carboxyl groups to the ester groups is approximately 1:1, (2) an anionic copolymer based on methacrylic acid and methylmethacrylate wherein the ratio of free carboxyl groups to the ester groups is approximately 1:2, (3) a copolymer based on acrylic and methacrylic acid esters with a low content of quaternary ammonium groups wherein the molar ratio of the ammonium groups to the remaining neutral methacrylic acid esters is 1:20, and (4) a copolymer based on acrylic and methacrylic acid esters with a low content of quaternary ammonium groups wherein the molar ratio of the ammonium groups to the remaining neutral methacrylic acid esters is 1:40, said copolymers being sold under the trademarks "Eudragit L," "Eudragit S," "Eudragit RL," and "Eudragit RS," respectively. Eudragit E™ is a cationic copolymer based on diethylaminoethyl methacrylate and neutral methacrylic acid esters. Eudragit NE™ is a neutral copolymer based on poly(meth)acrylates.

From among methacrylate or acrylate polymers, the preferred polymers are the Eudragit™ polymers, especially RS™, RL™, and NE™. These include, but are not limited to, Eudragit RS-100™, L-90™, NE-30™, L-100™, S-100™, E-100™, RL-100™, RS-100™, RS-30D™, E-100R™, and RTM™. In a highly preferred embodiment, the polymer suitable for the drug-containing matrix is Eudragit L-100™.

Suitable polymers may also include, but are not limited to, cellulose derivatives, ethyl cellulose, hydroxypropylmethyl cellulose, cellulose acetate phthalate, polysaccharides, guar gum, pectin, alginic acid and salts thereof, xanthan gum, gum tragacanth, starch, chitin, chitosan, proteins, polyamino acids, polypeptides, gelatin, polyglycolic acid, polylactic acid, polyglycolic-polylactic copolymers, cross-linked polysaccharides, and cross-linked proteins.

Adhesive materials include, but are not limited to, Eudragit S™ and Eudragit L™.

In a preferred embodiment, the adhesive material comprises Eudragit S™. In other embodiments, the adhesive material comprises solvents and carbopol, acrylates, or gums.

The same polymer can be used as the primary component of both the adhesive and non-adhesive layer. For example, Eudragit L™ does not self-adhere after it dries, even when wet with saliva. Therefore, when Eudragit L™ is used as the non-adhesive component, it must be adhered with an adhesive component. However, when Eudragit L™ is moistened with alcohol, this polymer forms an adhesive and therefore can be used to adhere a non-adhesive layer also comprised of Eudragit L™. Accordingly, Eudragit L™ and Eudragit S™ can form both the adhesive and non-adhesive component. Any of the Eudragit™ polymers can potentially form the non-adhesive layer.

In certain alternative embodiments, a polymer that is not self-adherent, for example dried Eudragit™, can be mixed with an adhesive component so that the patch does not need to be adhered separately. This applies to any of the dried Eudragit™ polymers. Adhesives that can be mixed with the non-adhesive polymer matrix include methacrylate polymers, polyacrylates, carbopol, hydroxy celluloses and polysaccharides such as hydroxypropyl cellulose, hydroxyethyl cellulose, hydroxypropylmethyl cellulose, pectin, calcium pectinate, alginic acid, calcium alginate, cellulose acetate phthalate, guar gum, gum tragacanth, gum acacia, other vegetable gums, and chitosan.

In further embodiments, the composition contains a release-adjusting agent. Release-adjusting agents include, but are not limited to arginine, lysine, pH adjusting agents such as sodium hydroxide, sodium carbonate, sodium bicarbonate, potassium hydroxide, potassium carbonate, and potassium bicarbonate. For embodiments in which Eudragit™ polymers, and particularly Eudragit L-100™ polymers, are used as a matrix for the drug, the release-adjusting agents that are preferred include, but are not limited to, sodium hydroxide, sodium carbonate, and sodium bicarbonate. The most highly preferred release-adjusting agent(s) for these polymers is sodium hydroxide.

The pharmaceutical oral patch can also contain a plasticizing agent. These include, but are not limited to, triethyl citrate, dibutylphthalate, diethylphthalate, acetyltriethyl citrate, tributyl citrate, acetyltetrabutyl citrate, triacetin, polyethylene glycol, castor oil, and other such plasticizers well known to those in the polymer art. The most highly preferred plasticizing agent(s) is triethyl citrate.

Figure 1:
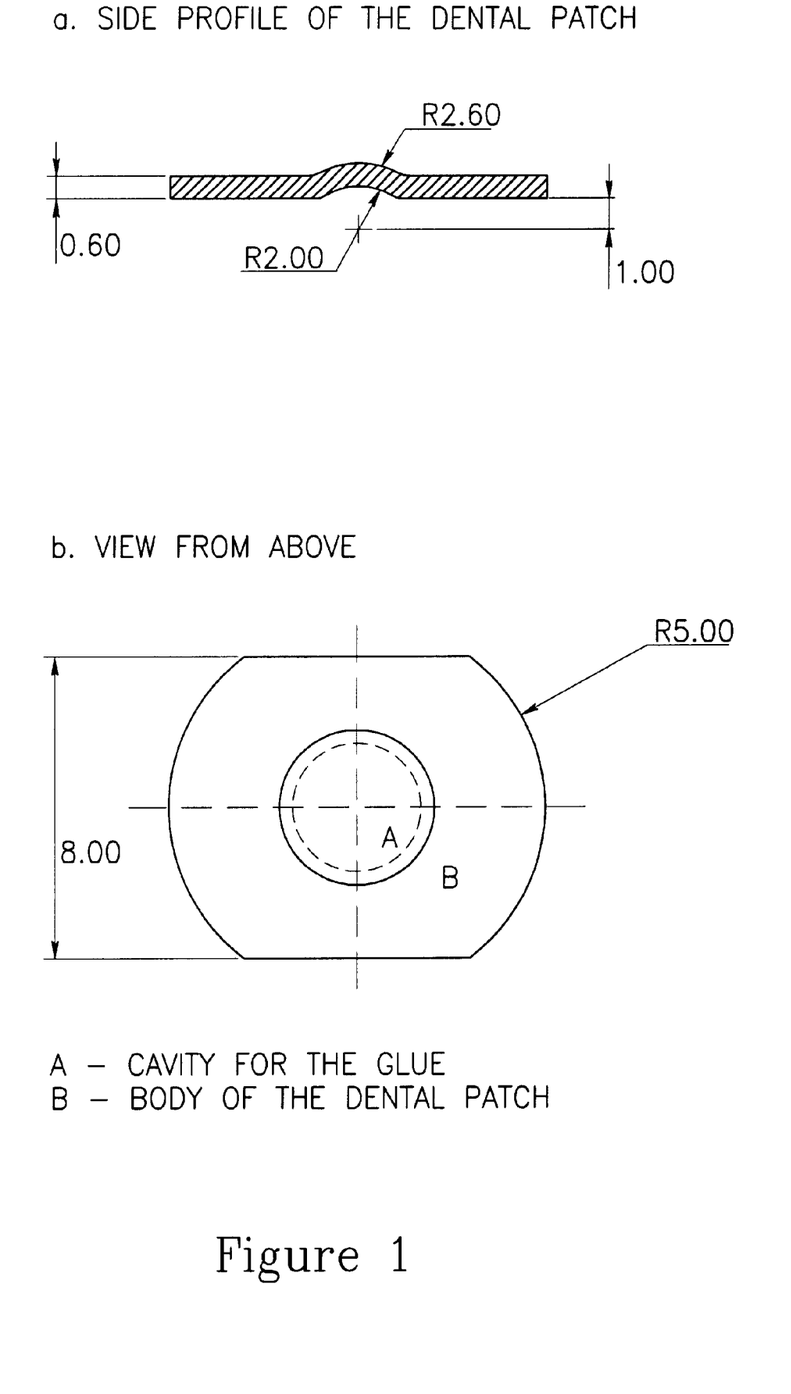
FIG. 1. Schematic view of a mold for the production of the controlled-release composition.

There is no limitation to the thickness of the adhesive layer. The thickness of the adhesive layer is determined by the size (weight) of the adhesive drop that has been put in the special cavity of the patch. See FIG. 1b, part A. The weight of the adhesive drop is preferably 10–30 mg, and especially 15–20 mg.

Although there is no limitation to the thickness of the sustained or controlled release layer, the thickness of the sustained-release layer is preferably no less than approximately 0.3 mm, preferably no less than approximately 0.5 mm, and no greater than approximately 4 mm, preferably no greater than approximately 1.5 mm. The especially preferred range is between 0.8–1.0 mm.

The composition is administered in appropriate sizes, typically having a surface area of about 30 mm$^2$ to 100 mm$^2$, and most preferably 60 mm$^2$. Whereas the material can be provided in any desired shape (oval, square, triangular, rectangular, etc.), a preferred shape is a tooth-like rectangle (see FIG. 1). Preferably, in square, triangle, rectangle, etc., the corners are rounded. The patch can be designed for one or more teeth, or other dental structure, such as dentures. Most preferably, the patch is designed for application to a single tooth.

Both the adhesive layer and a sustained-release layer can be modified into any shape and size, depending on the purposes of drug release. Thus, if large amounts of a drug are to be released, in addition to increasing the concentration in the sustained-release layer, a thicker layer can be applied. That is, the layer can be larger in size and/or greater in thickness.

The important consideration for shape and size is that the patch does not confer unusual sensation to the patient when applied, and can effectively release the desired pharmaceutically active agent at the desired levels and for the desired duration of time. For example, for the rapid release of a small amount of drug, a thin layer, in which the drug is dispersed, may be required.

The patch conforms to the contour of the tooth. The edges can be smoothed off so that there are no sharp edges that impart a foreign feel and result in the patch being dislodged by the patient. Edges, therefore, are preferably smooth and rounded. Since the material forming the patch is pliable when wet, it is soft so that it conforms to the contour of the tooth (or other hard structure in the oral cavity). Further, the patch is preferably not more than 3 or 4 mm thick.

The following considerations are important in choosing the site of application: (1) the salivary flow around the site; (2) the accessibility for application; (3) the comfort of the patient.

Both the adhesive and non-adhesive components are suitable to remain in the oral cavity for prolonged periods of time. In a preferred embodiment, the patch remains in the oral cavity between 6 to 8 hours. However, other embodiments can last for various desired periods of time.

The invention is also directed to a method for making the sustained-release compositions so that the rate of release can be adjusted in the final, solid form. The general procedure for forming the patch with Eudragit L™ or Eudragit S™ is as follows: The polymer is dissolved in a mixture of alcohol and water; sodium hydroxide is added to adjust the pH; triethyl citrate is added to plasticize the solid product; drug is added, and the mixture is stirred until dissolved; the mixture is molded; the material in the molds are dried.

The invention is also directed to methods for using the compositions of the present invention to release appropriate pharmaceutical agents in the oral cavity. Potentially, any pharmaceutically active agent can be released, although, as mentioned, the preferred agents are those that are poorly soluble or only moderately soluble in water.

In addition, potentially any condition can be treated by means of the release of a pharmaceutical from the patch. These are described in more detail below.

Preferred sites of application include but are not limited to the upper teeth.

The sites of action for the pharmaceutically active agents include the oral mucosa of the mouth and throat per se, systemic delivery via the oral mucosa, or localized delivery to one or more teeth.

When delivery is localized to the immediate area covered by the patch, the adhesive is chosen so that the agent can penetrate the adhesive and contact the covered area in effective amounts.

The amount of active agent included in the final, controlled release product can be determined by one skilled in the art without undue experimentation, and is generally from about 0.1% to about 35% by weight of the final product. The particular amount of the active agent included will, of course, depend upon the particular agent and its intended use.

The present invention can include other locally active agents, such as flavorants and sweeteners.

The flavoring agents may be natural or synthetic. They can be incorporated in the adhesive layer, the release layer, or both.

The flavoring agent is a common flavorant including wintergreen, peppermint, spearmint, menthol, fruit flavors, vanilla, cinnamon, various spices, or others known in the art.

Generally any flavoring or food additive, such as those described in *Chemical Used in Food Processing*, Pub. No. 1274, National Academy of Sciences, pages 63–258, can be used.

The amount of flavoring employed is normally a matter of preference subject to such factors as flavor type, individual flavor, and strength desired. Generally, the final product includes from about 0.1% to about 5% weight flavorant.

Sweeteners useful in the present invention include sucrose, aspartame, and saccharine. In general, sweeteners (when present) are included in an amount from about 0.001% to about 5.0% by weight of the final product.

Effective amounts of coloring agents (e.g., titanium dioxide, F.D. & C., and D. & C. dyes; see the Kirk-Othmer *Encyclopedia of Chemical Technology*, vol. 5, pp. 857–884), softeners, stabilizers, binders, odor-controlling agents, and preservatives can also be contained in the patch, as long as they do not impair adhesiveness or impede pharmacological effects from the release layer. For example, when both the adhesive and release layers are colorless, incorporation of a coloring matter in either makes it easy to distinguish the layers prior to application. It is understood that all optional additives can be in one or both layers of the patch.

The term "therapeutically effective amount" is intended to mean the amount of pharmaceutically active agent sufficient to produce the desired effect when released from the pharmaceutical oral patch described herein. These amounts are known in the art or may be determined by methods known in the art. The amounts depend upon the agents chosen and whether the site of action is the tooth per se, the oral mucosa (and the region of the oral mucosa), or systemic.

The upper limit on the amount of drug in the composition is determined by the properties of the polymeric matrix of the patch and the chemical interaction of the drug with the polymeric matrix.

The amount of active agent in the composition necessary to provide the desired amounts and concentration in the oral cavity can be determined by known methods. Thus, the concentration and the quantity of the agent per unit area of the patch (i.e., per square or cubic millimeter) can be varied independently in order to achieve a desired effect. Higher concentrations of agent contained in a dosage form of decreased thickness will result in an agent with fast onset and short duration. High concentrations of an agent contained in a dosage form of increased thickness (higher milligrams of agent per square or cubic millimeter) will result in potent effect with fast onset and long duration. Low concentrations of the agent in a dosage form of decreased thickness will result in mild effect with longer onset and short duration. Low concentrations of the agent contained in a dosage form of increased thickness will have mild effect with longer onset and longer duration. As shown in the above explanation, the ability to form thin or thick layers enables the practitioner of the invention to vary the dosage of the system as needed for particular anatomical sites of interest and according to the specific drug. The term "onset" is intended to mean the time needed to reach the desired concentration level of the pharmaceutical agent. It is used according to its normal and art-recognized meaning.

The term "duration", as used herein, means the period of time during which the desired concentration of pharmaceutical agent is delivered. This term is used according to its normal and art-recognized meaning.

The term "adhesive", as used herein, means an adhesive which attaches, and preferably strongly attaches, the release layer to teeth or other hard structures in the mouth such as dentures. To qualify as an adhesive, the substance must be capable of maintaining adhesion in the moist or wet environments of the oral cavity. It can also be "self-adhesive", in that it attaches to the site of interest without the need to reinforce its attachment by way of another adhesive. Thus, the term "adhesive" is used according to its normal and art-recognized meaning.

Adhesion can only be quantified with reference to a specific type of test or usage. It is not in itself a basic physical property, such as the surface free energy or the film thickness, whose measurement can be accomplished by a variety of methods. "Adhesion performance" must therefore be defined and measured in the context of the application of interest. Whether a given adhesive is effective for the oral cavity can be determined by a peel test in artificial saliva.

The strength of adherence can be measured by standard tests for measuring the force, for example in dynes per square centimeter, as disclosed in U.S. Pat. No. 4,615,697.

The term "subject" or "patient" is intended to include all mammals, preferably humans.

The term "patch", as used herein, is intended to mean a three-dimensional solid composition that can be adhered to teeth, or other hard structures in the mouth, such as dentures, by means of an adhesive portion or layer, which can contain a pharmaceutically active agent, and which can release the pharmaceutically active agent in effective amounts, for a desired period of time, from its site on the tooth into the oral cavity. The patch can comprise two essential and separate components that are immediately adjacent to each other.

These are an adhesive portion and a portion containing an active agent. The adhesive portion is used to adhere the other portion to the tooth or other hard dental structure. Alternatively, the drug-containing portion can, in some instances, self-adhere.

By "pharmaceutically active agent" is intended any chemical or biochemical that can be released from the pharmaceutical oral patch to prevent, cure, or ameliorate an undesirable physiological condition (see below). The term "drug" is used interchangeably herein. These terms are used according to their normal and art-recognized meanings.

Although any agent can be used, depending on the purpose of therapy, the following are exemplary:

1. anti-inflammatory, analgesic agents: content 0.1–5%
2. steroidal anti-inflammatory agents: content 0.002–0.5%
3. antihistamines: 0.1–2%
4. local anesthetics: 0.05–2%
5. bactericides and disinfectant: 0.01–10%
6. vasoconstrictors: 0.01–1%
7. hemostatics: 0.05–1%
8. chemotherapeutics: 0.05–1%
9. antibiotics: 0.001–10%
10. cosmetics
11. tooth desensitizing agents: 0.1–10%
12. antifungals: 0.1–10%
13. vasodilators: 0.1–10%
14. antihypertensives: 0.1–10%
15. antiemetics: 0.1–10%
16. antimigraine: 0.1–10%
17. antiarrhythmics: 0.1–10%
18. antiasthmatics: 0.1–10%
19. antidepressants: 0.1–10%
20. vaccines: 0.1–1%
21. peptides: 0.1–1%
22. hormones: 0.1–1%
23. Anti-proton pumps or H receptor blockers: 0.1–10%

Examples of anti-inflammatory, analgesic agents include acetaminophen, methyl salicylate, monoglycol salicylate, aspirin, mefenamic acid, flufenamic acid, indomethacin, diclofenac, alclofenac, diclofenac sodium, ibuprofen, flurbiprofen, fentizac, bufexamac, piroxicam, phenylbutazone, oxyphenbutazone, clofezone, pentazocine, mepirizole, and tiaramide hydrochloride.

Examples of steroidal anti-inflammatory agents include hydrocortisone, prednisolone, dexamethasone, triamcinolone acetonide, fluocinolone acetonide, hydrocortisone acetate, prednisolone acetate, methylprednisolone, dexamethasone acetate, betamethasone, betamethasone valerate, flumetasone, flouromotholone, budesonide and beclomethasone dipropionate.

Examples of antihistamines include diphenhydramine hydrochloride, diphenhydramine salicylate, diphenhydramine, chlorpheniramine hydrochloride, chlorpheniramine maleate, isothipendyl hydrochloride, tripelennamine hydrochloride, promethazine hydrochloride, and methdilazine hydrochloride.

Examples of local anesthetics include dibucaine hydrochloride, dibucaine, lidocaine hydrochloride, lidocaine, benzocaine, p-buthylaminobenzoic acid 2-(diethylamino) ethyl ester hydrochloride, procaine hydrochloride, tetracaine hydrochloride, chloroprocaine hydrochloride, oxyprocaine hydrochloride, mepivacaine, cocaine hydrochloride, and piperocaine hydrochloride.

Examples of bacteriocides and disinfectants include thimerosol, phenol, thymol, benzalkonium chloride, benzethonium chloride, chlorhexidine, providone iode, cetylpyridinium chloride, eugenol, and trimethylammonium bromide.

Examples of vasoconstrictors include naphazoline nitrate, tetrahydrozoline hydrochloride, oxymetazoline hydrochloride, phenylephrine hydrochloride, and tramazoline hydrochloride.

Examples of hemostatics include thrombin, phytonadione, protamine sulfate, aminocaproic acid, tranexamic acid, carbazochrome, carbaxochrome sodium sulfonate, rutin, and hesperidin.

Examples of chemotherapeutic drugs include vinblastine, cis-platin, 5-fluorouracil (5FU), methotrexate (MTX), 6 mercaptopurine (6MP), 1-β-D-arabinofuranosylcytosine (ara-C), mechlorethamine, chlorambucil, melphalan oxazaphosphorines, carboplatin, JM40, spiroplatin, tetraplatin, JM216, and taxol.

Examples of antibiotics include penicillin, meticillin, oxacillin, cefalotin, cefaloridin, erythromycin, lincomycin, tetracycline, chlortetracycline, oxytetracycline, metacycline, chloramphenicol, kanamycin, streptomycin, gentamicin, bacitracin, and cycloserine.

Examples of antifungal drugs include amphotericin, clotrimazole, econazole nitrate, fluconazole, griseofulvin, itraconazole, ketoconazole, miconazole, nystatin, terbinafine hydrochloride, undecenoio acid, and zinc undecenoate.

Examples of vasodilator drugs include buflomedil hydrochloride, bupheneine hydrochloride, naftidrofury oxalate, oxpentifylline, glyceryl trinitrate, isosorbide dinitrate, isosorbide mononitrate and pentaerythritol tetranitrate.

Examples of antihypertensive drugs include amlodipine, benazepril hydrochloride, captopril, clonidine hydrochloride, diazoxide, diltiazem hydrochloride, enalapril maleate, enalaprilat, felodipine, isradipine, nicardipine hydrochloride, nifedipine, atenolol, metoprolol tartarate, oxpenolol hydrochloride, propanolol hydrochloride and verapamil hydrochloride.

Examples of antiarrhythmic drugs include quinidine, quinidine salts, procainamide hydrochloride, lidocaine, and mexiletine hydrochloride.

Examples of antiemetic drugs include metoclopramide hydrochloride, nabilone, and ondansetron hydrochloride.

Examples of proton pump inhibitors or H receptor blockers include omeprazole, ranitidine and cimetidine.

Examples of antimigraine drugs include dihydroergotamine mesylate, ergotamine tartarate, sumatriptan succinate and other triptan drugs.

Examples of peptide or protein drugs include insulin, buserelin acetate, goserlin acetate, leuprorelin acetate, calcitonin, cyclosporin, gonadorelin, somastatin, vasopressin, oxytocin, interferon, and human growth hormone.

Examples of antidepressant drugs include fluoxetine hydrochloride, imipramine, maprotiline hydrochloride, phenelzine sulfate.

Examples of antiasthmatics include salbutamol, and terbutaline sulfate.

Examples of cosmetics include breath fresheners and tooth whiteners.

When release of the agent is localized to the teeth, preferred agents include tooth-whitening agents, such as carbamide peroxide and tooth-desensitizing agents, such as potassium nitrate and strontium chloride.

The conditions amenable to treatment with the patch described herein include, but are not limited to oral infections, lesions, low or high blood pressure, Helicobacter infections, pain, cough, migraine, vomiting, nausea, sleep apnea, gerd, reflux disease, and inflammation. Preferred conditions include yeast infections, periodontal diseases, snoring, oral ulcers or other lesions.

The invention will now be illustrated in greater detail with reference to the following examples, but it should be understood that these are not intended to limit the present invention.

EXAMPLES

Materials and Methods

Clotrimazole (or other poorly water soluble drugs)

Eudragit L-100™ and Eudragit S-100™ were purchased from the Rhom Pharma company.

Triethyl citrate NF (Eudraflex™) was purchased form the Rhom Pharma company.

Clotrimazole USP was purchased from the FIS (Fabrico Italian Sintestisi) company.

Ethanol USP and water USP were used throughout.

Preparation of Formulations

The general procedure for forming this patch was the dissolution of Eudragit L-100™ in a mixture of alcohol and water. Sodium hydroxide was added to adjust the pH. Triethyl citrate was added to the mixture to plasticize the resultant solid product. The drug of choice, e.g., clotrimazole, was added and the mixture stirred at room temperature until all dissolved. The resultant solution was metered into plastic molds that contained ~160 mg each and had the desired geometry of the patch. The solutions were dried under vacuum to form the finished product which has the dimensions of approximately 10 mm×8 mm×3 mm and weighs about 41 mg. The patch has a small well in the middle of one side for the tooth adhesive solution.

In a separate reaction the adhesive was prepared by dissolving Eudragit S™ in ethanol. The weight of the adhesive drop applied is generally 10–30 mg.

In Vitro Release

Patch formulations were stirred in 100 ml buffer (0.01M phosphate, pH=7.4) at room temperature. Samples of the solution were taken for analysis by HPLC or UV. Patch formulations were attached to a rod and buffer (0.01 M, Phosphate pH=7.4) was allowed to flow over one open surface at a rate of 0.5 ml/minute. Samples were taken for analysis by UV or HPLC.

In Vivo Release

Each volunteer attached two pharmaceutical oral patches of 5 mg clotrimazole to the buccal side of the upper teeth. No food or drink was allowed during the tests. Saliva samples were expectorated at given time intervals and tested for clotrimazole by HPLC. The patch was affixed to the tooth by using a drop of a solution of Eudragit S™ in ethanol.

Analysis by UV

Solutions from the release of clotrimazole were analyzed at a wavelength of 254 nm.

Solutions for the release of sodium salicylate were analyzed at a wavelength of 296 nm.

Solutions for the release of flurbiprofen were analyzed at a wavelength of 247 nm.

Analysis by HPLC

Analyses of the clotrimazole content in the patch and in the precursor solution were carried out according to standard analytical methods.

Results

Patch Formulation for Poorly Soluble Drugs

Examples of liquid polymer formulations for the pharmaceutical oral patches used for the delivery of clotrimazole, flurbiprofen and sodium salicylate are given in Table 1.

The pharmaceutical oral patch was formulated with clotrimazole as an example of a poorly water soluble drug, flurbiprofen as an example of a drug poorly soluble in water but soluble in buffer (neutral to slightly basic, i.e., pH≈7–8, with a high buffering capacity), and sodium salicylate as an example of a very soluble drug in both water and buffer.

TABLE 1

Liquid Polymer Formulations of Clotrimazole, Flurbiprofen and Sodium Salicylate for Pharmaceutical Oral Patch Formulation

| Formulation No.<br>Ingredient | 193-5<br>% W/W | 193-34<br>% W/W | 193-37<br>% W/W | 193-54B<br>% W/W | 193-72<br>% W/W | 193-81<br>% W/W | 193-86B<br>% W/W |
|---|---|---|---|---|---|---|---|
| Clotrimazole | 3 | 3 | 3 | 3 | 3 | | |
| Flurbiprofen | | | | | | | 3 |
| Sodium Salicylate | | | | | | 3 | |
| Polysorbate 80 | 1 | 3 | 3 | 2 | 2 | 2 | 2 |
| Methacrylic Acid copolymer A Eudragit L100 ™ | 14 | 14 | 14 | 12 | 12 | 12 | 12 |
| Triethylcitrate | 7 | 7 | 7 | 4 | 4 | 4 | 4 |
| Purified Water | 5 | 7 | 7 | 8 | 12 | 12.5 | 12.5 |
| Povidone | | | 0.5 | 0.5 | 0.5 | 0.5 | 0.5 |
| Sodium Hydroxide | 0.3 | 0.45 | 0.45 | 0.6 | 0.65 | 0.38 | |
| Glycerine | | 3 | 3 | 3 | 3 | 3 | 3 |
| Saccharin Sodium | | | | 0.1 | | | |
| Ethanol | 69.7 | 62.55 | 62.05 | 66.8 | 62.85 | 62.62 | 63 |

Experiment 1:

In Vitro Release of Clotrimazole

Clotrimazole (CTR) is an antifungal agent which is used to treat oral candidiasis. The infection is associated with HIV and other immune deficiencies. A conventional lozenge, mouthwash, or gel would be the simplest dosage form for the delivery of drugs through the mucosa or the oral cavity. But these dosage forms have the disadvantage of an initial burst of activity followed by a rapid decrease in concentrations to below therapeutic levels. Therefore, oral controlled-release devices are a viable alternative to the current conventional treatments.

Release profiles of CTR from patches that can adhere to the teeth were studied. Weighed amounts of the liquid polymer (160±5mg) were dried to form the pharmaceutical oral patch. The dry patches were inserted into 100 ml phosphate buffered saline (PBS) pH=7.4 and samples of 0.5 ml each were withdrawn at time intervals for HPLC analysis to determine the clotrimazole concentration. The cumulative percentage of the released clotrimazole was calculated.

TABLE 2

In Vitro Release From the Patch Produced From Formulation 193-34

| Time (hr) | % Release | % Release |
|---|---|---|
| 0 | 0 | 0 |
| 0.5 | 1.8 | 0.5 |
| 1 | 2.7 | 2.1 |
| 2 | 4.2 | 7.0 |
| 3 | 6.8 | 12.0 |
| 4 | 11.4 | 16.1 |
| 5 | 18.4 | 20.8 |

TABLE 3

In Vitro Release From the Patch Produced From Formulation 193-54B

| Time (hr) | % Release | % Release | % Release | % Release |
|---|---|---|---|---|
| 0 | 0 | 0 | 0 | 0 |
| 0.5 | 13.6 | 20.7 | 28.3 | 27.0 |
| 1 | 27.0 | 36.8 | 37.1 | 44.2 |
| 2 | 43.2 | 43.0 | 42.5 | 47.8 |
| 3 | 47.0 | 58.7 | 52.4 | 48.3 |
| 4 | 80.8 | 81.3 | 84.2 | 71.2 |
| 5 | 80.6 | 83.7 | 86.0 | 89.2 |
| 6 | 80.3 | 85.0 | 95.2 | 89.5 |
| 7 | 95.0 | 96.0 | 96.0 | 94.4 |

TABLE 4

In Vitro Release From the Patch Produced From Formulation 193-72

| Time (hr) | % Cum. Rel. | % Cum. Rel. |
|---|---|---|
| 0 | 0 | 0 |
| 0.5 | 10.8 | 12.6 |
| 1 | 25.6 | 32.7 |
| 2 | 72.3 | 36.1 |
| 3 | 75.0 | 92.7 |
| 4 | 96.1 | 97.4 |
| 5 | 99.0 | 99.8 |

One can see that by using a release adjusting agent, such as sodium hydroxide, in the formulations (see Table 1), one can exert control over the release profile. The sodium hydroxide alters the molar concentration of acidic carboxylic groups in the Eudragit™ matrix thereby changing its solubility. This alters the erosion of the matrix and hence the release profile. As shown in the tables which are given above the release patterns are changed by the addition of sodium hydroxide. Formulations with lower sodium hydroxide release very slowly (20% in five hours) while formulations with more NaOH (the percent molar ratio to the Eudragit™ acid groups was raised from 15.6% in formulation 193-34 to 27% in formulation 193-72 ) gave complete release in five hours. One can conclude that by adjusting the molar ratio of NaOH to COOH groups the release can be adjusted and controlled to levels desired.

Experiment 2:

In vivo release of clotrimazole

The in vivo release from the patches made from three formulations of differing molar ratios of NaOH were tested in vivo. Formulation 193-5 has a low level of NaOH (percent molar ratio of 11.5%) and the patch made therefrom is expected to release drug even more slowly than the patch made from formulation 193-34.

Formulation 193-37 is similar to 193-34 in its molar ratio of neutralization.

Formulation 193-72 was also tested.

The measured clotrimazole levels in the saliva are summarized in Table 5.

TABLE 5

In Vivo Release From the Patches Produced From Formulation 193-37, 193-72 and 193-5

| Formulation Time (hr) | 193-37 Conc (ppm) | 193-37 Conc (ppm) | 193-72 Conc (ppm) | 193-5 Conc (ppm) |
|---|---|---|---|---|
| 0 | 0 | 0 | 0 | 0 |
| 0.5 | 3.2 | 130 | 43.8 | 2 |
| 1 | 46 | 28 | 93.6 | 5 |
| 1.5 | | | | 4 |
| 2 | 44 | 21 | 51.6 | 2 |
| 3 | 107 | 32 | 18.5 | |
| 3.5 | | 55 | | |
| 4 | 30 | | 13.4 | |
| 5 | 8 | | | |
| 6 | 10 | 7 | | |

One can see that the in vivo release is also greatly affected by the release adjusting agent. Patches from formulation 193-5 releases the drug too slowly.

Formulation 193-37 gave theoretically efficacious levels of the clotrimazole over a period of six hours as did formulation 193-72. An analysis of the remaining drug in the remnants of the pharmaceutical oral patch after the experiment showed that essentially all the drug remained in formulation 193-5, ~60% in formulation 193-37 and ~3% in formulation 193-72. A total dose of only 10 mg of clotrimazole is capable of delivering clinically significant levels of clotrimazole in saliva for at least 6 hours.

Experiment 3:

In vitro release of sodium salicylate and flurbiprofen

Sodium salicylate and flurbiprofen are therapeutical substances of the category of analgesics and anti-inflammatory agents. We chose to use sodium salicylate and flurbiprofen in our formulations to demonstrate the influence of the solubility (in water) of the active ingredient on the release profile of the substance since flurbiprofen is only slightly soluble while sodium salicylate is very soluble. Patches formed from formulations 193-81 and 193-86B from Table 1 were tested in vitro for drug release. Results are tabulated in Tables 6 and 7.

TABLE 6

In Vitro Release From Patches Produced From Formulation 193-81 Containing Sodium Salicylate:

| Time (hr) | % Cum Rel | % Cum Rel | % Cum Rel |
|---|---|---|---|
| 0 | 0 | 0 | 0 |
| 0.25 | 98 | 96 | 95 |

TABLE 6-continued

In Vitro Release From Patches Produced From
Formulation 193-81 Containing Sodium Salicylate:

| Time (hr) | % Cum Rel | % Cum Rel | % Cum Rel |
|---|---|---|---|
| 0.5 | 100 | 100 | 100 |
| 1 | 100 | 100 | 100 |
| 2 | 100 | 100 | 100 |

TABLE 7

In Vitro Release From Patches Produced From
Formulation 193-86B Containing Fluribiprofen:

| Time (hr) | % Cum Rel | % Cum Rel | % Cum Rel |
|---|---|---|---|
| 0 | 0 | 0 | 0 |
| 0.5 | 57 | 53 | 56 |
| 1 | 94 | 90 | 91 |
| 2 | 97 | 95 | 97 |

One can clearly see that the more soluble the drug the faster the release of the active agent is from this matrix.

What is claimed is:

1. A dual-component oral composition for providing sustained controlled release of one or more pharmaceutically active agents therefrom, comprising an adhesive component, said adhesive component comprising at least one polymer, said adhesive component being effective for adhering to teeth or dentures, immediately adjacent to and adhered to a non-adhesive component, said non-adhesive component containing at least one polymer, at least one plasticizer, and one or more pharmaceutically active agents, and from which non-adhesive component said one or more agents are released into the oral cavity in therapeutically active amounts when said adhesive component is adhered to teeth, dentures, or other hard surface in said oral cavity, both components being suitable to remain in the oral cavity for a period of time necessary to allow release of a therapeutically effective amount of said one or more agents into the oral cavity, wherein said adhesive component and said non-adhesive component are substantially degradable so that said composition is degradable.

2. The composition of claim 1, wherein said adhesive component comprises an adhesive selected from the group consisting of carbopol, acrylates, polyacrylates, polysaccharides, polymethacrylates and gums.

3. The composition of claim 1, wherein said nonadhesive component comprises a sustained-release polymer selected from the group consisting of polyacrylate, polymethacrylate, cellulose derivatives, ethylcellulose, hydroxypropylmethyl cellulose, cellulose acetate phthalate, polysaccharide, guar gum, pectin, alginic acid and salts thereof, xanthan gum, gum tragacanth, gum arabic, starch, chitin, chitosan, proteins, polyamino acids, polypeptides, gelatin, polyglycolic acid, polylactic acid, polyglycolic-polylactic copolymers, cross-linked polysaccharides, and cross-linked proteins.

4. The composition of claim 3, wherein said polymethylacrylate polymer is a polymer selected from the group consisting of a dimethylaminoethylacrylate/ ethylmethacrylate copolymer, said copolymer based on acrylic and methacrylic acid esters with a low content of quaternary ammonium groups, wherein the molar ratio of the ammonium groups to the remaining neutral (meth) acrylic acid esters is approximately 1:20 said polymer corresponding to USP/NF "Ammonio Methacrylate Copolymer Type A", an ethylmethacrylate/ chlorotrimethylammoniumethyl methacrylate copolymer, said copolymer based on acrylic and methacrylic acid esters with a low content of quaternary ammonium groups wherein the molar ratio of the ammonium groups to the remaining neutral (meth)acrylic acid esters is 1:40, said polymer corresponding to USP/NF "Ammonio Methacrylate Copolymer Type B"; a dimethylaminoethylmethacrylate/ methylmethacrylate and butylmethacrylate copolymer, a copolymer based on neutral methacrylic acid esters and dimethylaminoethyl methacrylate esters wherein the polymer is cationic in the presence of acids and an ethylacrylate and methylacrylate/ethylmethacrylate and methyl methacrylate copolymer, said copolymer being a neutral copolymer based on neutral methacrylic acid and acrylic acid esters.

5. The polymer of claim 4, wherein said polymer is an anionic copolymer based on methacrylic acid and methylmethacrylate wherein the ratio of free carboxyl groups to the ester groups is approximately 1:1.

6. The composition of claim 1, wherein said adhesive component comprises one or more pharmaceutically active agents and from which adhesive component said one or more agents are released into the oral cavity in therapeutically effective amounts when said adhesive component is adhered to teeth, dentures, or other hard surface in said oral cavity.

7. A method of making the non-adhesive component of claim 1, comprising:

(i) mixing one or more polymers in a solvent comprising alcohol and water;

(ii) stirring to form a uniform mixture;

(iii) adding a release adjusting agent;

(iv) adding a plasticizer, (v) adding a pharmaceutical agent; and (vi) allowing the mixture to dry in a molded form, wherein said one or more polymers are selected from the group consisting of a dimethylaminoethyl- acrylate/ ethylmethacrylate copolymer, said copolymer based on acrylic and methacrylic acid esters with a low content of quaternary ammonium groups, wherein the molar ratio of the ammonium groups to the remaining neutral (meth) acrylic acid esters is approximately 1:20. said polymer corresponding to USP/NF "Ammonio Methacrylate Copolymer Type A", an ethylmethacrylate/ chlorotrimethylammoniumethyl methacrylate copolymer said copolymer based on acrylic and methacrylic acid esters with a low content of quaternary ammonium groups wherein the molar ratio of the ammonium groups to the remaining neutral (meth)acrylic acid esters is 1:40, said polymer corresponding to USP/NF "Ammonio Methacrylate Copolymer Type B" a dimethylaminoethylmethacrylate/ methylmethacrylate and butylmethacrylate copolymer, a copolymer based on neutral methacrylic acid esters and dimethylaminoethyl methacrylate esters wherein the polymer is cationic in the presence of acids, and an ethylacrylate and methylacrylate/ethylmethacrylate and methyl methacrylic copolymer, said copolymer being a neutral copolymer based on neutral methacrylic acid and acrylic acid esters.

8. The method of claim 7, wherein said polymer is an anionic copolymer based on methacrylic acid and methylmethacrylate wherein the ratio of free carboxyl groups to the ester groups is approximately 1:1.

9. The method of claim 7 wherein said pharmaceutical agent is selected from the group consisting of clotrimazole, amphotericin, isosorbide dinitrate, isosorbide mononitrate, nifedipine, omeprazole, piroxicam, ondansetron hydrochloride, salbutamol, a steroid, dihydroergotamine mesylate, and methotrexate.

10. A method for administering a pharmaceutically active agent in the oral cavity comprising affixing the composition of any of claims 1–5 to teeth or dentures of a subject and releasing said agent in said oral cavity.

11. A method for administering a pharmaceutically active agent in the oral cavity comprising affixing a single layered composition for providing sustained or controlled release of a pharmaceutically active agent therefrom, said composition being a substantially degradable adhesive and effective for adhering to teeth or dentures, from which adhesive composition said agent is released into said oral cavity in therapeutically active amounts when said adhesive composition is adhered to teeth, dentures, or other hard surface in said oral cavity, said composition being suitable to remain in said oral cavity for a period of time necessary to allow release of a therapeutically effective amount of said agent into said oral cavity, and wherein said composition consists essentially of one or more pharmaceutically active agents, one or more plasticizers, and one or more polymers selected from the group consisting of an anionic copolymer based on methacrylic acid and methylmethacrylate wherein the ratio of free carboxyl groups to the ester groups is approximately 1:1 and an anionic copolymer based on methyacrylic acid and methylmethacrylate wherein the ratio of free carboxyl groups to the ester groups is approximately 1:2.

12. A method for administering a pharmaceutically active agent in the oral cavity comprising affixing a single layered composition for providing sustained or controlled release of a pharmaceutically active agent therefrom, said composition being a substantially degradable adhesive and effective for adhering to teeth or dentures, from which adhesive composition said agent is released into said oral cavity in therapeutically active amounts when said adhesive composition is adhered to teeth, dentures, or other hard surface, said composition being suitable to remain in the oral cavity for a period of time necessary to allow release of a therapeutically effective amount of said agent into said oral cavity, and wherein said composition consists essentially of one or more pharmaceutically active agents, one or more plasticizers, at least one agent conferring adhesiveness and a polymer wherein said polymer is selected from the group consisting of a dimethylaminoethyl-acrylate/ethylmethacrylate copolymer, said copolymer based on acrylic and methacrylic esters with a low content of quaternary ammonium groups, wherein the molar ratio of the ammonium groups to the remaining neutral (meth)acrylic acid esters is approximately 1:20, said polymer corresponding to USP/NF "Ammonio Methacrylate Copolymer Type A"; an ethylmethacrylate/chlorotrimethylammoniumethylmethacrylate copolymer, said copolymer based on acrylic and methacrylic acid esters with a low content of quaternary ammonium groups wherein the molar ratio of the ammonium groups to the remaining neutral (meth)acrylic acid esters is 1:40, said polymer corresponding to USP/NF "Ammonio Methacrylate Copolymer Type B"; a dimethylaminoethylmethacrylate/methylmethacrylate and butylmethacrylate copolymer, a copolymer based on neutral methacrylic acid esters and dimethylaminoethyl methacrylate esters wherein the polymer is cationic in the presence of acids; and an ethylacrylate and methylacrylate/ethylmethacrylate and methyl methacrylate copolymer, said copolymer being a neutral copolymer based on neutral methacrylic acid and acrylic acid esters.

13. A dual-component oral composition for providing sustained or controlled release of a pharmaceutically effective agent therefrom, said composition comprising adhesive and nonadhesive components, wherein said adhesive component contains at least one polymer and is comprised of one or more adhesive layers and said nonadhesive component is comprised of one or more nonadhesive layers, said adhesive component comprising one or more adhesive layers that are effective for adhering to teeth or dentures, immediately adjacent to and adhered to said one or more non-adhesive layers, said one or more non-adhesive layers comprising at least one polymer, at least one plasticizer and one or more pharmaceutically active agents, and wherein said one or more agents are released into the oral cavity from said one or more non-adhesive layers in therapeutically effective amounts when said one or more adhesive layers are adhered to teeth, dentures, or other hard surfaces, said adhesive and nonadhesive layers being suitable to remain in the oral cavity for a period of time necessary to allow release of a therapeutically effective amount of said one or more agents into the oral cavity, and wherein said one or more adhesive and non-adhesive layers are substantially degradable so that said composition is degradable.

14. The composition of claim 13 wherein said pharmaceutically active agents comprise one or more of the same or different drugs.

15. The composition of claim 13 wherein said one or more nonadhesive layers comprises one or more of sweeteners, flavorants, release adjusting agents, pH adjusting agents, emulsifiers, solubility adjusting agents and plasticizers.

16. The composition of claim 13 wherein said one or more adhesive layers comprises one or more of sweeteners, flavorants, release adjusting agents, pH adjusting agents, emulsifiers, solubility adjusting agents and plasticizers.

17. The composition of claim 13 wherein said one or more adhesive layers, said one or more non-adhesive layers, or both, comprise one or more Eudragit™ polymers.

18. The composition of claim 13 wherein said one or more adhesive layers comprise one or more pharmaceutically active agents and from which adhesive layers said one or more agents are released into the oral cavity in therapeutically effective amounts when said one or more adhesive layers are adhered to teeth, dentures, or other hard surface in said oral cavity.

19. The composition of claim 18 wherein said pharmaceutically active agents comprise one or more of the same or different drugs.

* * * * *